US008289329B2

(12) United States Patent
Warntjes

(10) Patent No.: US 8,289,329 B2
(45) Date of Patent: Oct. 16, 2012

(54) VISUALIZATION OF QUANTITATIVE MRI DATA BY QUANTITATIVE TISSUE PLOT

(76) Inventor: Marcel Warntjes, Linköping (SE)

( * ) Notice: Subject to any disclaimer, the term of this patent is extended or adjusted under 35 U.S.C. 154(b) by 786 days.

(21) Appl. No.: 12/429,321

(22) Filed: Apr. 24, 2009

(65) Prior Publication Data

US 2009/0267945 A1    Oct. 29, 2009

Related U.S. Application Data

(60) Provisional application No. 61/047,893, filed on Apr. 25, 2008.

(51) Int. Cl.
G06T 11/20 (2006.01)
(52) U.S. Cl. ........................................ 345/440
(58) Field of Classification Search ............... 345/440
See application file for complete search history.

(56) References Cited

U.S. PATENT DOCUMENTS

| | | | |
|---|---|---|---|
| 4,634,979 A | 1/1987 | Riederer et al. | |
| 4,641,095 A | 2/1987 | Riederer | |
| 4,881,033 A | 11/1989 | Denison et al. | |
| 5,410,250 A * | 4/1995 | Brown | 324/309 |
| 5,486,763 A | 1/1996 | Alfano | |
| 5,644,232 A * | 7/1997 | Smith | 324/304 |
| 6,823,205 B1 | 11/2004 | Jara | |
| 6,917,199 B2 | 7/2005 | Jara | |
| 7,002,345 B2 | 2/2006 | Jara | |
| 7,145,336 B2 * | 12/2006 | Brown | 324/309 |
| 7,170,290 B2 * | 1/2007 | Miyoshi | 324/309 |
| 7,280,681 B2 * | 10/2007 | Meyer | 382/128 |
| 7,782,056 B2 * | 8/2010 | Noterdaeme et al. | 324/309 |
| 2002/0016543 A1 * | 2/2002 | Tyler | 600/410 |
| 2007/0167727 A1 | 7/2007 | Menezes et al. | |
| 2008/0108894 A1 * | 5/2008 | Elgavish et al. | 600/420 |
| 2008/0114234 A1 * | 5/2008 | Gering | 600/411 |
| 2010/0127704 A1 | 5/2010 | Warntjes | |
| 2011/0018537 A1 | 1/2011 | Warntjes | |

FOREIGN PATENT DOCUMENTS

WO    2008/082341 A1    7/2008

OTHER PUBLICATIONS

"Simulation of MRI Cluster PLots and Application to Neurological Segmentation", Simons et al.,Magnetic Resonance Imaging, vol. 14, pp. 73-92, 1996.*
Generating T1 and T2 Maps of MRI Images http://home.caregroup.org/departments/radiology/basic_mr/matlab/matlab.html Software updated Sep. 1, 2002.*
R. Maitra et al., Bayesian Reconstruction in Synthetic Magnetic Resonance Imaging, Proc. SPIE, 1998, pp. 39-47, vol. 3459.
M. Prastawa et al., Synthetic Ground Truth for Validation of Brain Tumor MRI Segmentation, Med Image Comput Comput Assist Interv., 2005, pp. 26-33, 8 (Pt 1).
K.H. Cheng et al., In-vivo Tissue Characterization of Brain by Synthetic MR Proton Relaxation and Statistical Chisquares Parameter Maps, Proc. 8th Symposium on Computer-Based Medical Systems, 1995, pp. 338-345, IEEE.
U.S. Appl. No. 12/620,874, inventor Marcel Warntjes, filed Nov. 18, 2009, and to documents cited therein.

* cited by examiner

*Primary Examiner* — Ryan R Yang
(74) *Attorney, Agent, or Firm* — Potomac Patent Group PLLC

(57) ABSTRACT

In a magnetic resonance (MR) imaging display system, the values of at least two quantitative MR parameters for a given Region of Interest (ROI) are displayed and dynamically updated when the ROI is changed.

36 Claims, 4 Drawing Sheets

VISUALIZATION OF QUANTITATIVE MRI DATA BY QUANTITATIVE TISSUE PLOT

TECHNICAL FIELD

The present invention relates to a method and a system for displaying of a plot of at least two quantitative Magnetic Resonance (MR) parameters.

BACKGROUND

Magnetic Resonance Imaging (MRI) can generate cross-sectional images in any plane (including oblique planes). Medical MRI most frequently relies on the relaxation properties of excited hydrogen nuclei in water and fat. When the object to be imaged is placed in a powerful, uniform magnetic field the spins of the atomic nuclei with non-integer spin numbers within the tissue all align either parallel to the magnetic field or anti-parallel. The output result of an MRI scan is an MRI contrast image or a series of MRI contrast images.

In order to understand MRI contrast, it is important to have some understanding of the time constants involved in relaxation processes that establish equilibrium following RF excitation. As the high-energy nuclei relax and realign, they emit energy at rates which are recorded to provide information about their environment. The realignment of nuclear spins with the magnetic field is termed longitudinal relaxation and the time (typically about 1 sec) required for a certain percentage of the tissue nuclei to realign is termed "Time 1" or T1. T2-weighted imaging relies upon local dephasing of spins following the application of the transverse energy pulse; the transverse relaxation time (typically <100 ms for tissue) is termed "Time 2" or T2. On the scanner console all available parameters, such as echo time TE, repetition time TR, flip angle $\alpha$ and the application of preparation pulses (and many more), are set to a certain value. Each specific set of parameters generates a particular signal intensity in the resulting images depending on the characteristics of the measured tissue.

Image contrast is then created by using a selection of image acquisition parameters that weights signal by T1, T2 or no relaxation time PD ("proton-density images"). Both T1-weighted and T2-weighted images as well as PD images are acquired for most medical examinations.

In contrast imaging the absolute signal intensity observed in the image has no direct meaning; it is rather the intensity difference, the contrast, between different tissues that lead to a diagnosis. The TE, TR, $\alpha$ and pre-pulses are chosen such that it provides the best contrast for a specific application. This implies that for each desired contrast a separate image has to be taken. This in turn will make a complete examination rather time consuming and demanding for the patient. Also, it will become costly since equipment and other resources can only be used for one patient at the time. If the known parameter settings do not provide the desired contrast, insufficient for diagnosis, it is far from straightforward to achieve an improvement.

An existing method and system for visualizing MRI images are described in the international patent publication no. WO 2008/082341 A1, which is incorporated herein by reference.

There is a constant desire to improve methods for visualizing MRI images.

SUMMARY

It is an object of the present invention to provide an improved method of visualizing MRI images and also to provide an apparatus and a computer program for performing the visualizing.

This object and others are obtained by the method and apparatus as set out in the appended claims.

In accordance with the present invention the values of the at least two quantitative MR parameters for a given Region of Interest (ROI) is displayed and dynamically updated when the ROI is changed.

The invention also extends to an apparatus adapted to execute the method. The method can in one embodiment be software implemented.

BRIEF DESCRIPTION OF THE DRAWINGS

The present invention will now be described in more detail by way of non-limiting examples and with reference to the accompanying drawings, in which.

DETAILED DESCRIPTION

Figure 1:
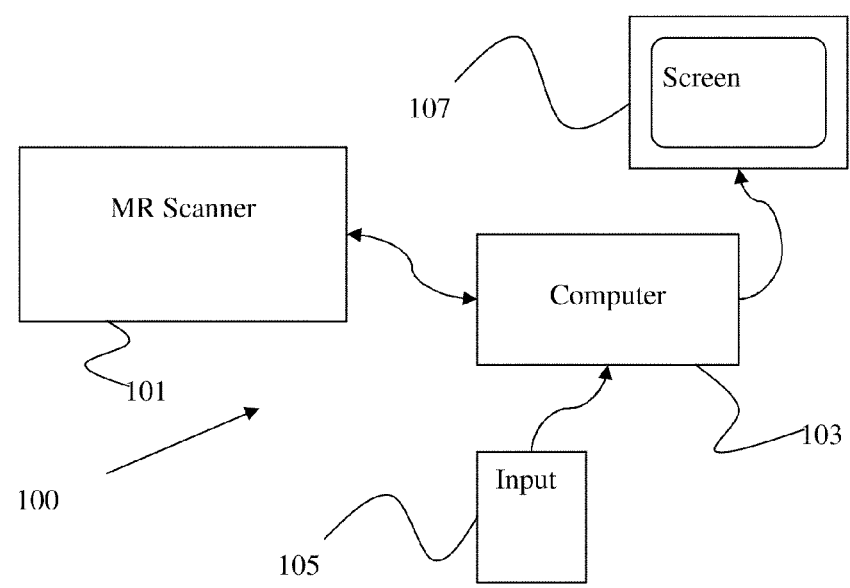
FIG. 1 is a general view of a MRI system.

In FIG. 1 a general view of a setup of a MRI system 100 is depicted. The system 100 comprises a MR scanner 101. The MR scanner is operative to generate MRI data by means of scanning a living object. The MR scanner is further connected to a computer 103 for processing data generated by the scanner 101. The computer comprises a central processor unit coupled to a memory and a number of input and output ports for receiving and outputting data and information. The computer 103 receives input commands from one or several input devices generally represented by an input device 105. The input device may be one or many of a computer mouse, a keyboard, a track ball or any other input device. The computer 103 is further connected to a screen 107 for visualizing the processed scanner data as a contrast image. The MRI system can be made to operate and display images in response to a computer program loaded into the memory of the system and executed by the computer. The computer program can be stored on any suitable storage media such as a ROM, a disc or similar.

In Magnetic Resonance Imaging (MRI), the Magnetic Resonance Imaging parameters T1 relaxation, T2 relaxation and Proton Density PD can be measured on an absolute scale.

For human tissue these parameters typically are in the order 300-4500 ms for T1, 50-1000 ms for T2 and 0-100% water for PD. Both T1 and T2 depend on the field strength.

These absolute parameters can be visualized in a 2-dimensional quantitative plot containing two of the three, e.g. T1 as a function of T2 or T1 as a function of PD. Alternatively the relaxation rate can be taken on the axes where the rate R1 corresponds to 1/T1 and R2 to 1/T2.

Since each tissue has its unique combination of absolute parameters the typical position of a tissue can be indicated in this plot. Since all measurements contain noise this position indication will have a certain size, i.e. correspond to some area/cluster within the plot. All image pixels that contain a specific tissue will be positioned inside this tissue cluster indication. If a pixel contains two kinds of tissue it will have a position on a line between the two respective cluster positions. These lines can be indicated as well in the quantitative tissue plot. Reference values for tissue clusters can be obtained from a group of healthy volunteers.

A quantitative tissue plot cannot be based on conventional T1- and T2-weighted images since the scaling of these images is arbitrary and hence the reference clusters cannot be set.

Figure 2:
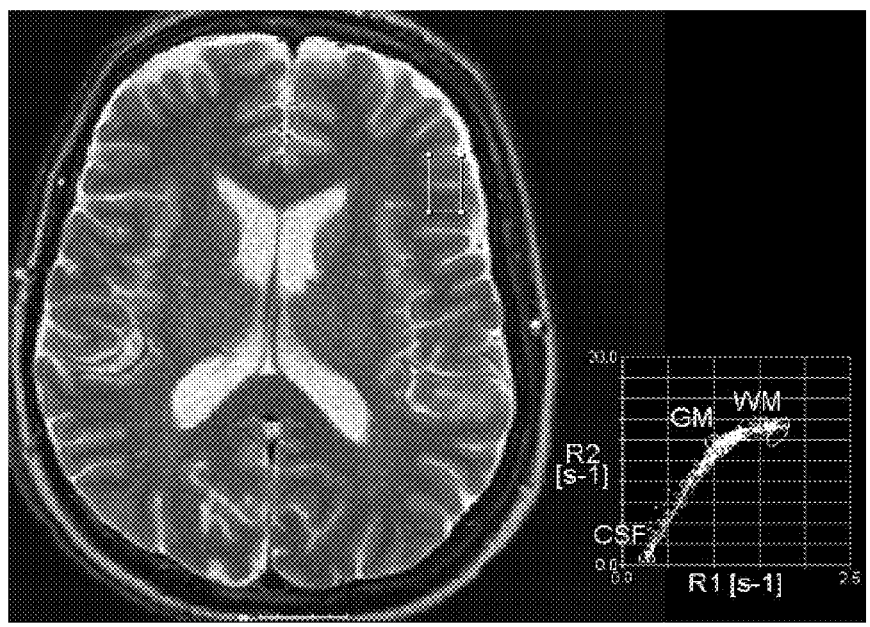
FIG. 2 is a an example for visualization of quantitative MRI data by means of a quantitative tissue plot.

In FIG. 2 an example for visualization of quantitative MRI data by means of a quantitative tissue plot is shown. A conventional or quantitative MR image of the brain is displayed together with an indication of a Region of Interest (ROI) which covers a number of pixels up to the complete image. In the example depicted in FIG. 1 it is the small square depicted on the brain. The absolute values of the pixels inside the ROI are displayed in the quantitative tissue plot on the right in FIG. 2.

In the example depicted in FIG. 2, the absolute pixel values R1 and R2 are used as coordinates in that plot. Other parameters may be plotted on the axes as described above. By plotting two parameters for a given ROI against each other a user viewing the resulting plot can, with the help of the indicated tissue cluster position and the connecting lines, verify whether the indicated pixels contain healthy tissue or pathological tissue. In this case all pixels are on the lines between Cerebro-spinal fluid (CSF) to Grey Matter (GM) and on the line Grey Matter to White Matter (WM), meaning there is no indication of pathology inside the ROI.

In accordance with another exemplary embodiment R1 can be plotted as a function of PD. This plot would indicate clearly the relation between R1 and water content of the tissue. For the brain this is a line crossing the axes at PD=105% and R1=4.5. Another benefit of a plot of R1 against PD would be the indication of fat which has completely different values than water and hence will be far of the mentioned line. Using these plots will assist software to segment the various tissue types automatically.

In accordance with one embodiment the plot can be set to display a normal deviation of the values from the reference positions of healthy tissue and the lines in between. This indicates the normal variation of the tissue values due to noise and natural inhomogeneity of the tissue. Any pixel that is outside these indicated regions has a high probability to be pathological.

In accordance with one embodiment of the present invention, the plot can display typical reference positions for one or many pathology tissue types, e.g. the typical position of an MS lesion or a tumor.

Also the system plotting the plot can be adapted to display the path of normal behavior of a tissue during a dynamic process, e.g. the change in R1 and R2 of a tissue during contrast media uptake or the change of R1 and R2 of water as a function of temperature, or the change of R1 and R2 during the development of a neonates as a function of age.

In accordance with one embodiment the imaging system as described herein can be adapted to enable a user to interactively change the reference indications in the quantitative plot. For example the user can change from a brain reference indicating brain tissue clusters into an abdomen reference indicating for example liver, muscle, fat and bile clusters.

Figure 3:
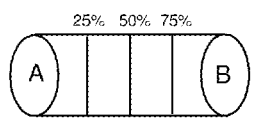
FIG. 3 is a plot displaying lines between typical reference positions for specific tissues.

In accordance with another embodiment of the present invention, the plot can display lines between the typical reference positions for specific tissues. Such a view is shown in FIG. 3 as exemplary tissues A and B. These two lines indicate the borders of an area where the data most probably contains partially tissue A and partially tissue B.

Also there may be additional lines perpendicular to these two border lines (ticks) that indicate a specific partial volume percentage. In FIG. 3 there are three ticks indicating 25%, 50% and 75% partial volume of tissue A and B.

In accordance with another embodiment of the present invention the plot can display color gradients to indicate partial volume. More intense color indicates higher probability of a certain tissue type. Using the plot a data point from a quantitative MR measurement can be assigned a color. This color translation can be used for MR images to indicate the partial volume of a certain tissue type in the image. An example of color indication of partial volume is shown in FIG. 4

Figure 4:
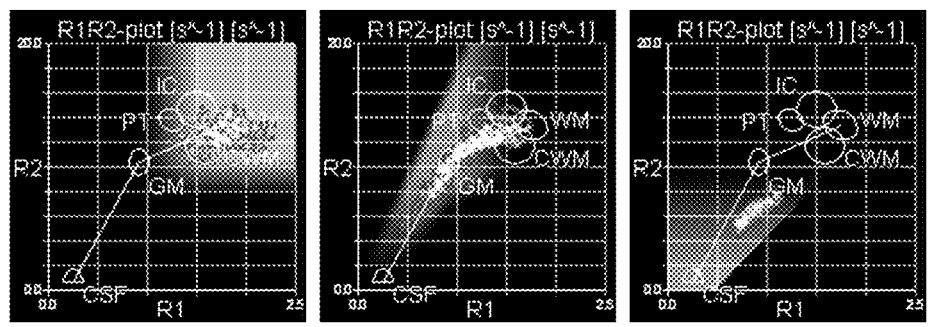
FIG. 4 is an exemplary view of a quantitative plot with the relaxation rates R1 and R2 for the brain with color indication for tissue partial volume.
Figure 4:
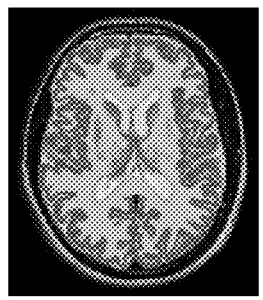

In FIG. 4 an exemplary view of a quantitative plot with the relaxation rates R1 and R2 for the brain with color indication for tissue partial volume is shown. The color gradients (blue, green, and purple in the plots from left to right, which are indicated by light grey shading in the black-and-white figure) show the partial volume probability regimes of white matter (WM), grey matter (GM) and cerebrospinal fluid (CSF), respectively, where more intense colors indicate higher partial volume estimations. The reference cluster regions of healthy CSF, GM, subcortical WM, central WM (CWM), putamen (PT) and internal capsule (IC) are also shown. The WM color gradients from the R1R2 plot are used for a translation from measurement data of R1 and R2 into a color overlay over an MR image of the brain. The color overlay indicates partial volume of WM.

Figure 5:
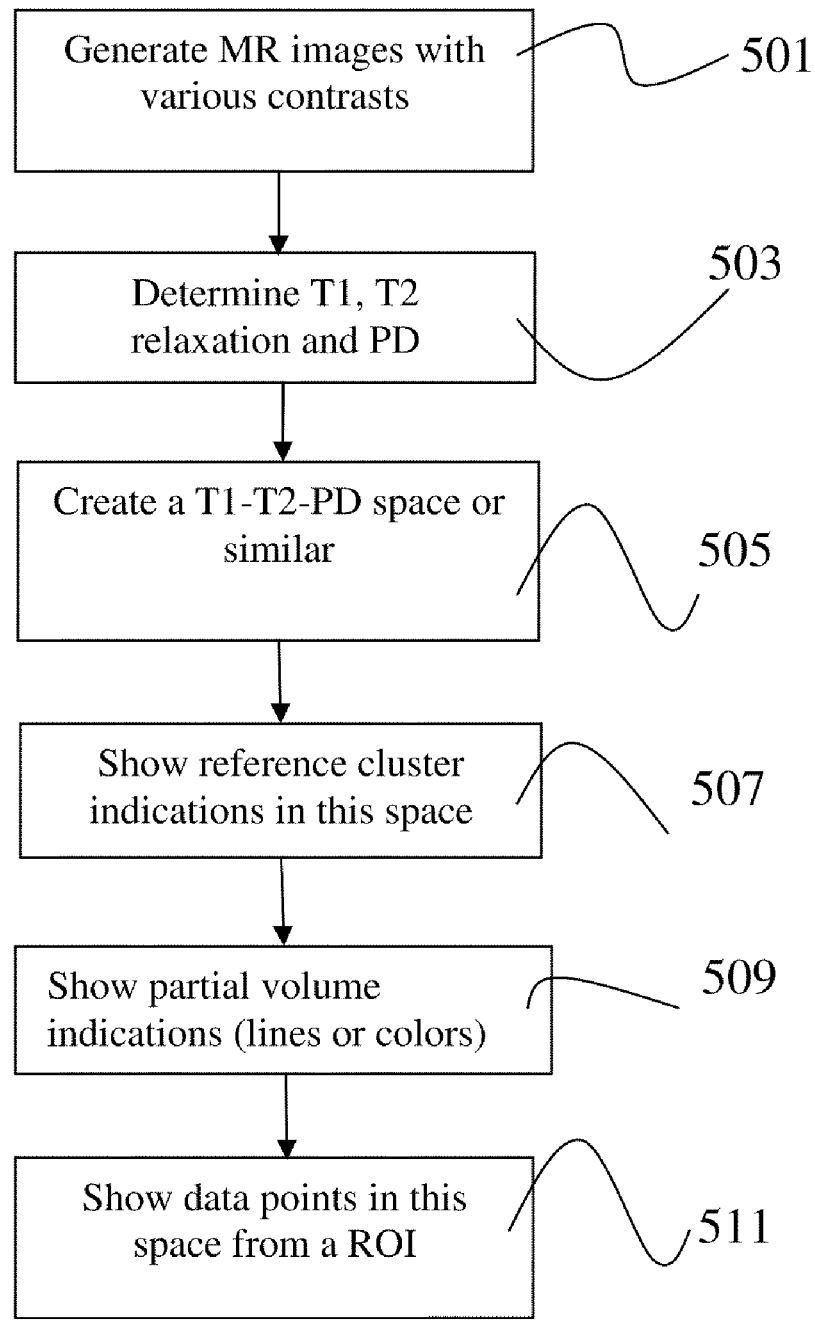
FIG. 5 is a flowchart illustrating steps performed when generating a non-physical MR image.

In FIG. 5 a flowchart illustrating some procedural steps that can be performed when visualizing an MR image in accordance with the above is depicted. First in a step 501 MR images with various contrasts are generated. Next, in a step 503, the set of images generated in step 501 are used to determine different MR parameters of the image such as T1, T2 and PD. For example the MR parameters for each pixel or voxel of the image are determined. Next, in a step 505, the values are displayed in as suitable space such as a plot on a computer screen or some other display device. Next, in a step 507 reference clusters of known values for different tissue types are displayed in the space. Thereupon in a step 509 partial values are also displayed in the space, for example by using lines or by color-coding depending on how the space is represented in a display. Next, in a step 511 a user can select a particular region of interest in the MR image and the values of the pixels/voxels of that region are displayed in the space.

What is claimed is:

1. A method of displaying a plot of at least two quantitative magnetic resonance (MR) parameters against each other, wherein values of the at least two quantitative MR parameters for a given Region of Interest (ROI) are displayed according to an absolute scale and dynamically updated when the ROI is changed.

2. The method of claim 1, wherein the MR parameters correspond to at least one of T1 and T2 relaxation or proton density or relaxation rate R1 and R2, where R1=1/T1 and R2=1/T2.

3. The method of claim 1, wherein reference positions corresponding to specific healthy tissue are shown in the plot.

4. The method of claim 3, wherein the healthy tissue corresponds to white matter and grey matter in a brain or muscle and fat in an abdomen.

5. The method of claims 3, wherein lines between the reference positions indicate an area where pixels contain two types of tissue are shown in the plot.

6. The method of claim 5, wherein lines between the reference positions indicate a position of a specific partial volume percentage of two types of tissue are shown in the plot.

7. The method of claim 5, wherein color gradients indicate the position of a specific partial volume percentage of a single tissue, where each tissue has its own unique color.

8. The method of claim 7, wherein the color gradients in the plot are used to generate a color overlay over the MR images to indicate the estimated partial volume of each tissue type.

9. The method of claim 1, wherein reference positions corresponding to specific pathologic tissue are shown in the plot.

10. The method of claim 9, wherein a combination of specific reference positions of pathological tissue indicates a disease or syndrome.

11. The method of claim 1, wherein the plot displays a path of normal behavior of a tissue during a dynamic process.

12. The method of claim 11, wherein the dynamic process is the change in R1 and R2 of tissue during contrast media uptake, or the change of R1 and R2 of water as a function of temperature, or the change of R1 and R2 during the development of a neonates as a function of age.

13. An apparatus for displaying a plot of at least two quantitative magnetic resonance (MR) parameters against each other on a display according to an absolute scale, wherein the apparatus is configured to dynamically update and display values of the at least two quantitative MR parameters for a given Region of Interest (ROI) when the ROI is changed.

14. The apparatus of claim 13, wherein the apparatus is adapted to display MR parameters corresponding to at least one of T1 and T2 relaxation or proton density or relaxation rate R1 and R2, where R1=1/T1 and R2=1/T2.

15. The apparatus of claims 13, wherein the apparatus is adapted to display reference positions corresponding to specific healthy tissue on the display.

16. The apparatus of claim 15, wherein healthy tissue corresponds to white matter and grey matter in a brain or muscle and fat in an abdomen.

17. The apparatus of claim 15, wherein the apparatus is adapted to display lines between the reference positions to indicate an area where pixels contain two types of tissue.

18. The apparatus of claim 17, wherein the apparatus is adapted to display lines between the reference positions to indicate the position of a specific partial volume percentage of two types of tissue.

19. The apparatus of claim 18, wherein the apparatus is adapted to display MR images in combination with one or several color overlays where color intensity is based on predetermined color gradients that indicate estimated tissue partial volume, where each tissue has its own unique color.

20. The apparatus of claim 18, wherein the apparatus is adapted to display color gradients to indicate a position of a specific partial volume percentage of a single tissue, where each tissue has its own unique color.

21. The apparatus of claim 13, wherein the apparatus is adapted to display reference positions corresponding to specific pathologic tissue on the display.

22. The apparatus of claim 21, wherein the apparatus is adapted to display a combination of specific reference positions of pathological tissue to indicate a disease or syndrome.

23. The apparatus of claim 13, wherein the apparatus is adapted to display a path of normal behavior of a tissue during a dynamic process.

24. The apparatus of claim 23, wherein the dynamic process is a change in R1 and R2 of tissue during contrast media uptake, or a change of R1 and R2 of water as a function of temperature, or a change of R1 and R2 during the development of a neonates as a function of age.

25. A non-transitory storage medium for storing a computer program, where the computer program comprises computer program segments that when executed on a computer causes the computer to display a plot of at least two quantitative magnetic resonance (MR) parameters against each other, wherein values of the at least two quantitative MR parameters for a given Region of Interest (ROI) are displayed according to an absolute scale and dynamically updated when the ROI is changed.

26. The non-transitory storage medium of claim 25, wherein the MR parameters correspond to at least one of T1 and T2 relaxation or proton density or relaxation rate R1 and R2, where R1=1/T1 and R2=1/T2.

27. The non-transitory storage medium of claim 25, wherein reference positions corresponding to specific healthy tissue are shown in the plot.

28. The non-transitory storage medium of claim 27, wherein the healthy tissue corresponds to white matter and grey matter in a brain or muscle and fat in an abdomen.

29. The non-transitory storage medium of claim 27, wherein lines between the reference positions indicate an area where pixels contain two types of tissue are shown in the plot.

30. The non-transitory storage medium of claim 29, wherein lines between the reference positions indicate a position of a specific partial volume percentage of two types of tissue are shown in the plot.

31. The non-transitory storage medium of claim 29, wherein color gradients indicate a position of a specific partial volume percentage of a single tissue, where each tissue has its own unique color.

32. The non-transitory storage medium of claim 31, wherein the color gradients in the plot are used to generate a color overlay over the MR images to indicate the estimated partial volume of each tissue type.

33. The non-transitory storage medium of claim 25, wherein reference positions corresponding to specific pathologic tissue are shown in the plot.

34. The non-transitory storage medium of claim 33, wherein a combination of specific reference positions of pathological tissue indicates a disease or syndrome.

35. The non-transitory storage medium of claim 25, wherein the plot displays a path of normal behavior of a tissue during a dynamic process.

36. The non-transitory storage medium of claim 35, wherein the dynamic process is a change in R1 and R2 of tissue during contrast media uptake, or a change of R1 and R2 of water as a function of temperature, or a change of R1 and R2 during development of a neonate as a function of age.

\* \* \* \* \*